(12) United States Patent
Gil et al.

(10) Patent No.: US 8,754,005 B2
(45) Date of Patent: Jun. 17, 2014

(54) COLOR-CHANGING COMPOSITION AND MATERIAL

(75) Inventors: JunMo Gil, DaeJoen (KR); Ning Wei, Roswell, GA (US); JinHo Ryu, Yongin-si (KR); Xuedong Song, Alpharetta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 73 days.

(21) Appl. No.: 13/596,605

(22) Filed: Aug. 28, 2012

(65) Prior Publication Data

US 2014/0066870 A1   Mar. 6, 2014

(51) Int. Cl.
| | |
|---|---|
| *B41M 1/40* | (2006.01) |
| *B41M 5/00* | (2006.01) |
| *A61F 13/42* | (2006.01) |
| *A61L 15/56* | (2006.01) |
| *G01N 21/81* | (2006.01) |
| *G01N 31/22* | (2006.01) |

(52) U.S. Cl.
USPC .................. 503/205; 106/31.32; 604/361

(58) Field of Classification Search
CPC ... A61F 13/42; A61F 2013/429; A61L 15/56; G01N 21/81; G01N 31/222; B41M 1/40; B41M 5/00
USPC .................. 503/205; 106/31.32; 604/361
See application file for complete search history.

(56) References Cited

U.S. PATENT DOCUMENTS

| | | | |
|---|---|---|---|
| 3,937,864 | A | 2/1976 | Kohmura et al. |
| 5,130,290 | A | 7/1992 | Tanimoto |
| 5,197,958 | A | 3/1993 | Howell |
| 5,415,434 | A | 5/1995 | Kawashima |
| 2003/0089270 | A1 | 5/2003 | Chien et al. |
| 2007/0270773 | A1 | 11/2007 | Mackey |
| 2008/0279253 | A1 | 11/2008 | MacDonald |
| 2009/0157024 | A1 | 6/2009 | Song |
| 2010/0030173 | A1 | 2/2010 | Long et al. |
| 2010/0159599 | A1 | 6/2010 | Song et al. |
| 2010/0248959 | A1 | 9/2010 | Hirai et al. |
| 2011/0104023 | A1 | 5/2011 | Otomo et al. |
| 2011/0144603 | A1 | 6/2011 | Song |
| 2011/0152805 | A1 | 6/2011 | Song |

FOREIGN PATENT DOCUMENTS

| | | |
|---|---|---|
| EP | 0 097 220 A2 | 1/1984 |
| JP | 04-085374 A | 3/1992 |
| JP | 10077437 A | 3/1998 |
| WO | WO 2007/004629 A1 | 1/2007 |
| WO | WO 2012/023070 A2 | 2/2012 |
| WO | WO 2012/023071 A2 | 2/2012 |

*Primary Examiner* — Bruce H Hess
(74) *Attorney, Agent, or Firm* — Amy L. Kading

(57) ABSTRACT

The present disclosure relates to a color-changing composition and to a substrate having the color-changing compositions disposed thereon. The color-changing composition includes a leuco dye, a color-developer and a desensitizer. The color-changing composition changes from a colorless or largely colorless composition to color upon being wetted with an aqueous liquid. The color-changing composition remains colorless or largely colorless prior to exposure to high relative humidity conditions.

18 Claims, 3 Drawing Sheets

COLOR-CHANGING COMPOSITION AND MATERIAL

The present disclosure relates to a color-changing composition that is color-appearing in the presence of an aqueous liquid. In particular, the present disclosure pertains to a medium or an ink that remains colorless or largely colorless in high relative humidity and when wetted with an aqueous liquid, changes to higher intensity color.

BACKGROUND OF THE DISCLOSURE

Many products, including consumer and professional products, are more effectively used by an end user when the product includes a feature that can communicate or signal to the user a particular condition or a relative level or degree of use. An example of a visual, communicative feature is a wetness indicator made by applying a color-changing composition to a substrate. Wetness indicators can either indicate a change in condition or a degree of use through a change from colorless or largely colorless to colored or through a change in color intensity.

Exemplary conditions that could be monitored using a wetness indicator include physical conditions such as the presence of moisture and chemical conditions. Exemplary consumer products that could be more effective and deliver more benefits to end users by incorporating a suitable wetness indicator include absorbent articles, such as diapers, training pants, incontinence products, or feminine hygiene pads. Other exemplary consumer products include facial tissues, bath tissue, paper towels, household cleaning items and personal cleaning wipes. Exemplary professional products that could be more effective and deliver more benefits to end users by incorporating a suitable wetness indicator include products for medical use, safety garments, industrial cleaning products and nonwoven materials. Many consumer and professional products have synthetic polymeric substrates incorporated therein which often serve as liquid barriers.

Wetness indicators are well known and are available in various forms. Desirable performance attributes include stability in high relative humidity conditions and the ability to change from colorless or largely colorless to colored when it is most meaningful to indicate a change to the user, that is, upon being wetted with an aqueous liquid. It may also be desirable for the wetness indicator to have a distinct color change to aid the user in identifying the physical condition change in the product.

Standard room temperature and standard relative humidity are the conditions that are maintained in most homes and work areas. Standard room temperature and standard relative humidity is typically accepted as the temperature range of 20° C. to 25° C. at a range of 40% to 60% relative humidity (American Society of Heating, Refrigerating and Air-Conditioning Engineers, Inc. (ASHRAE)). Most color-changing compositions, where the color change is due to the color-changing composition being wetted with an aqueous liquid, are stable under standard temperature and relative humidity conditions. Without being bound by theory, it is believed that color-changing compositions where the color change is due to the color-changing composition being wetted with an aqueous liquid are no longer able to maintain their original color state when standard relative humidity conditions are exceeded. For example, a color-changing composition printed on a polymeric substrate of a diaper may experience premature exposure to conditions other than standard room temperature and standard relative humidity during the manufacturing process, warehouse storage, product distribution and end user storage up until the time of use. Premature exposure of the color-changing composition to levels of relative humidity higher than standard relative humidity can affect the indicator efficacy such that the end user will not receive visual communication of the change when the color-changing composition is wetted with an aqueous liquid. This happens when the wetness indicator prematurely experiences a color change prior to being wetted with an aqueous liquid.

While the color-changing compositions known in the art provide certain benefits, there remains a need for a color-changing composition that remains stable in high relative humidity conditions. There also remains a need for the color-changing composition to change to a higher intensity color when the color-changing composition becomes wetted with an aqueous liquid. There remains a need for a color-changing composition that is durable, non-leachable, water-resistant, and water-insoluble. There further remains a need for a color-changing composition that can be applied to substrates using a printing technique at room temperature. In addition to the needs identified above, there are unmet needs associated with using color-changing materials as components of personal care absorbent articles, such as disposable diapers. In particular, there is a need for a color-changing composition that maintains its efficacy when applied to an outer cover material.

SUMMARY OF THE DISCLOSURE

In an embodiment, a color-changing composition comprises a leuco dye, a color-developer, a desensitizer, a binder, and an organic solvent. The desensitizer is selected from the group consisting of tetraalkyl ammonium carboxylate, tetraalkyl ammonium hydroxide, tetraalkyl ammonium halide and combinations thereof.

In an embodiment, a color-changing material comprises a substrate and a color-changing composition disposed on the substrate. The color-changing composition comprises a leuco dye, a color-developer, a desensitizer, and a binder. The desensitizer comprises tetraalkyl ammonium carboxylate, tetraalkyl ammonium hydroxide, tetraalkyl ammonium halide or combinations thereof.

In an embodiment, a disposable absorbent article has an absorbent core adjacent an outer cover of the disposable absorbent article. A color-changing composition is disposed between the absorbent core and the outer cover. The color-changing composition comprises a leuco dye, a color-developer, a desensitizer, and a binder. The desensitizer comprises tetraethyl ammonium acetate, tetramethyl ammonium acetate, tetrabutyl ammonium acetate or combinations thereof.

DETAILED DESCRIPTION

Figure 1A:
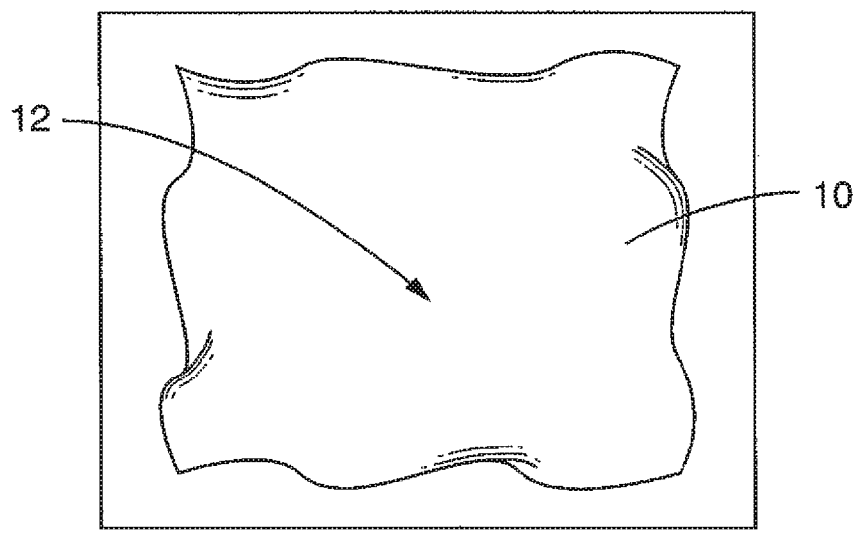
FIG. 1A shows a substrate having an ink composition of the present disclosure deposited thereon and dried, where the ink has a largely colorless appearance.

The present disclosure will be expressed in terms of its various components, elements, constructions, configurations, arrangements and other features that may also be individually or collectively referenced by the term, "embodiment(s)" of the disclosure, or other similar terms. It is contemplated that the various forms of the present disclosure may incorporate one or more of its various features and embodiments, and that such features and embodiments may be employed in any desired, operative combination thereof.

It should be noted that, when employed in the present disclosure, the terms "comprise", "comprising" and other derivatives from the root term "comprise" are intended to be open-ended terms that specify the presence of any stated features, elements, integers, steps, or components, and are not intended to preclude the presence or addition of one or more other features, elements, integers, steps, components or groups thereof.

The present disclosure relates to a color-changing composition that remains stable in high relative humidity conditions. The color-changing composition changes to a higher intensity color when the composition is exposed to a change in its immediate physical or chemical environments as a result of being wetted with an aqueous liquid. The disclosure also includes color-appearing compositions stable in high relative humidity being components of a color-changing material. The composition can be applied to a substrate surface by conventional printing techniques.

The present disclosure involves an irreversible color-appearing composition that contains at least three major components: (1) a leuco dye or a combination of leuco dyes, (2) a color-developer or a combination of color-developers that can form colored complexes with leuco dyes by donating hydrogen cations, and (3) a desensitizer to temporarily block the effect of the color-developer so that the leuco dye remains colorless or largely colorless until wetted with an aqueous liquid. All of the foregoing components are dissolved together in a volatile organic solvent medium to form a solution. Polymeric binder materials may also be added to the color-changing composition.

Other additives may be used such as to adjust the physical properties of the color-changing composition. The color-changing composition may contain reagents to adjust the viscosity of the solution, or may include chemistry to improve adhesion of the color-changing composition to certain substrate surfaces upon drying. The color-changing composition may further include chemistry that tailors the subsequent wettability of the color-changing composition on the substrate surface.

The color-changing composition of the disclosure is initially colorless or largely colorless and changes to a higher intensity color when the color-changing composition is printed and dried upon a substrate and subsequently wetted with an aqueous liquid. The color intensity is judged by the naked human eye. The various levels of color intensity as judged by the naked human eye are usually described as low, lower, lowest, medium, high, higher, or highest either when describing the initial color intensity formed after the printed and dried color-changing composition has been wetted with an aqueous liquid or when compared to printed and dried color-changing compositions of the same color.

Leuco dyes are generally referred to as colorless or pale-colored dyes because the dye molecules can acquire two forms, one of which is largely colorless. Without being bound by theory, it is believed that the color-developer functions as a Lewis acid which withdraws electrons from the leuco dye molecule, acting as a proton donator, to generate a conjugated system. Also without being bound by theory, it is believed that suitable non-Lewis acid color-developers may provide hydrogen ions which result in changes to the conjugated systems of the leuco dye molecule through a halochromatic mechanism. Hence, the developed leuco dye manifests color from an originally colorless state due to the newly formed conjugated systems having the ability to absorb photons of visible light.

The leuco dye is an electron-donating dye which may be selected from phthalide or fluoran type dyes. Phthalide type leuco dyes include arylmethane phthalides, such as triarylmethane phthalides and diarylmethane phthalides, monoheterocyclic substituted phthalides such as, heterocyclic substituted phthalides, diarylmethylazaphthalides, bisheterocyclic substituted phthalides, 3-heterocyclic substituted azaphthalides, 3,3-bisheterocyclic substituted azaphthalides, alkenyl substituted phthalides, bridged phthalides and bisphthalides. Specific examples of phthalide type leuco dyes include: 3,3-bis(p-dimethylaminophenyl)-6-dimethylaminophthalide; 3,3-bis(p-dimethylaminophenyl)phthalide; 3-(p-dimethylaminophenyl)-3-(1,2-dimethylindol-3-yl)phthalide; 3-(p-dimethylaminophenyl)-3-(2-methylindol-3-yl)phthalide; 3,3-bis(1,2-dimethylindol-3-yl)-5-dimethylaminophthalide; 3,3-bis(1,2-dimethylindol-3-yl)-6-dimethylaminophthalide; 3,3-bis(9-ethylcarbazol-3-yl)-6-dimethylaminophthalide; 3,3-bis(2-phenylindol-3-yl)-6-dimethylaminophthalide; 3-p-dimethylaminophenyl-3-(1-methylpyrrol-3-yl)-6-dimethylaminophthalide; 3,3-bis(1-n-butyl-2-methyl-3-indolyl)phthalide (Red 40); 3,3-bis(4-diethylamino-2-ethoxyphenyl)-4-azaphthalide; 3,3-bis(4-diethylphenyl)-4-azaphthalide (GN2); 3-(4-diethylamino-2-ethoxyphenyl)-3-(1-ethyl-2-methyl-3-indolyl)-4-azaphthalide (Blue 63); 4,4'-bisdimethylaminobenzhydryl benzyl ether; N-halophentlleucoauramine; N2; 4,5-trichlorophenyl-leucoauramine; rhodamine-B-anilinolactam; rhodamine B lactam; rhodamine-(p-nitroanilino)lactam; and rhodamine-(o-chloroanilino)lactam. Fluoran leuco dyes include 3-dimethylamino-7-methoxyfluoran; 3-diethylamino-6-methoxyfluoran; 3-diethylamino-7-methoxyfluoran; 3-diethylamino-7-chlorofluoran; 3-diethylamino-6-methyl-7-chlorofluoran; 3-di-ethylamino-6,7-dimethylfluoran; 3-(N-ethyl-p-toluidino)-7-methylfluoran; 3-diethylamino-7-(N-acetyl-N-methylamino)fluoran; 3-diethylamino-7-(N-methylamino)fluoran; 3-diethylamino-7-dibenzylaminofluoran; 3-diethylamino-7-(N-methyl-N-benzylamino)fluoran; 3-diethylamino-7-(N-chloroethyl-N-methylamino)fluoran; 3-diethylamino-7-N-diethylaminofluoran; 3-(N-ethyl-p-toluidino)-6-methyl-7-phenylaminofluoran; 3-(N-ethyl-p-toluidino)-6-methyl-7-(p-toluidino)fluoran; 3-diethylamino-6-methyl-7-phenylaminofluoran; 3-dibutylamino-6-methyl-7-phenylaminofluoran; 3-diethylamino-7-(2-carbomethoxyphenylamino)fluoran; 3-(N-cyclohexyl-N-methylamino)-6-methyl-7-phenylaminofluoran; 3-pyrrolidino-6-methyl-7-phenylaminofluoran; 3-piperidino-6-methyl-7-phenylaminofluoran; 3-diethylamino-6-methyl-7-(2,4-dimethylamino)fluoran, 3-diethylamino-7-(o-chlorophenylamino)fluoran; 3-dibutylamino-7-(o-chlorophenylamino)fluoran; 3-pyrrolidino-6-methyl-7-(p-butylphenylamino)fluoran; 3-(N-methyl-N-n-amylamino)-6-methyl-7-phenylaminofluoran; 3-(N-ethyl-N-n-amylamino)-6-methyl-7-phenylaminofluoran; 3-(N-ethyl-N-isoamylamino)-6-methyl-7-phenylaminofuluoran; 3-(N-methyl-N-n-hexylamino)-6-methyl-7-phenylaminofluoran; 3-(N-ethyl-N-n-hexylamino)-6-methyl-7-phenylaminofluoran; 3-(N-ethyl-N-β-ethylhexylamino)-6-methyl-7-phenylaminofluoran, 3',6'-dimethoxyfluoran; N-acetylauramine; N-phenylauramine; 3,6-dihexyloxyfluoran; 2'-chloro-6'-aminofluoran; 3,6-bis(diethylamino)fluoran-γ-(4'-nitro)-anilinolactam; 2'-chloro-6'-diethylaminofluoran; 6-diethylaminobenzo[c]-fluoran; 2-(phenyliminoethanedilidene)-3,3- trimethyl-indoline; 3',6'-bis-(diphenylamino)fluoran; crystal violet lactone; benzoyl leucomethylene blue; ethyl leucomethylene blue; methoxybenzoyl leucomethylene blue; 2',6'-bis(diethyl-amino)fluoran; malachite green lactone; 2'-anilino-3' methyl-6'-(N-methyl-N-n-propylamino)fluoran; 3-cyclohexyl methylamino-6-methyl-7-anilinofluoran; 1,3,3-trimethyl-indolino-7'-chloro-β-naphthospiropyran and di-β-naphthospiropyran. The leuco dyes useful in this disclosure are not limited to those exemplified above.

The color-changing compositions of the disclosure include a leuco dye in an amount from about 0.1% to about 20.0% of the total weight of the color-changing composition. Desirably, the color-changing compositions of the disclosure include a leuco dye in an amount from about 5.0% to about 10.0% of the total weight of the color-changing composition. The color-changing compositions of the disclosure may include more than one leuco dye. One or more leuco dyes that have visually different colors may be combined or leuco dyes having the same visual color may be combined.

The color-changing composition of the disclosure includes at least one electron-withdrawing color-developer or a combination of color-developers that can form colored complexes with leuco dyes. The color-developer provides a hydrogen cation, $H^+$, from the phenolic group. The hydrogen cation migrates from the color-developer to activate the aryl ester group of the opened ring leuco dye to form a conjugate system. The amount of color-developer of the disclosure can be present from about 0.1% to about 17.0% of the total weight of the color-changing composition. Desirably, the color-changing compositions of the disclosure include a color-developer in an amount from about 5.0% to about 8.0% of the total weight of the color-changing composition.

Examples of suitable color-developers include bisphenol A, zinc chloride, zinc salicylate, and phenol resins. Other examples of color-developing materials to be used conjointly with the leuco dyes may include: 4-tert-butylphenol; α-naphthol; β-naphthol; 4-acetylphenol; 4-tert-octylphenol; 4,4'-sec-butylidenephenol; 4-phenylphenol; 4,4'-dihydroxydiphenylmethane; 4,4'-isopropylidene diphenol; hydroquinone; 4,4'-cyclohexylidene diphenol; 4,4-dihydroxy diphenylsulfide; 4,4'-thiobis(6-tert-butyl-3-methylphenol); 4,4'-dihydroxydiphenyl sulfone; hydroquinone monobenzyl ether; 4,4-hydroxybenzophenone; 2,4-dihydroxybenzophenone; 4,4'-dihydroxybenzophenone; 2,4,4'-trihydroxybenzophenone; 2,2',4,4'-tetrahydroxybenzophenone; dimethyl 4-hydroxyphthalate; methyl 4-hydroxybenzoate; ethyl 4-hydroxybenzoate; propyl 4-hydroxybenzoate; sec-butyl 4-hydroxybenzoate; pentyl 4-hydroxybenzoate; phenyl 4-hydroxybenzoate; benzyl 4-hydroxybenzoate; tolyl 4-hydroxybenzoate; chlorophenyl 4-hydroxybenzoate; phenylpropyl 4-hydroxybenzoate; phenethyl 4-hydroxybenzoate; p-chlorobenzyl 4-hydroxybenzoate; p-methoxybenzyl 4-hydroxybenzoate; novolak type phenol resins; phenol polymers and like phenol compounds.

The color-changing composition of the disclosure includes at least one desensitizer. The desensitizer interrupts the formation of color by temporarily blocking hydrogen cation migration from the color-developer to the leuco dye. Tetraalkyl ammonium carboxylate or tetraalkyl ammonium hydroxide are effective desensitizers in high relative humidity conditions as these desensitizers minimize acid element residue. The tetraalkyl ammonium group stabilizes the phenolic anion of the color-developer in solution by ionic charge-charge neutralization. The desensitizer provides small-sized carboxylate or hydroxide elements with scavenging phenolic hydrogen cations to generate small volatile molecules, such as water, $H_2O$, or acetic acid, $CH_3CO_2H$. The small water or acetic acid molecules can be evaporated during the drying step of the printing process used to apply the composition onto a substrate. The desensitizer provides for a color-changing composition, when printed on a substrate, that is stable in high relative humidity conditions of up to 85% relative humidity and temperatures exceeding 40° C. The general formula of the desensitizer as tetraalkyl ammonium carboxylate in the form of acetate is $R_4N^+$ OAc. The general structure of the desensitizer as tetraalkyl ammonium carboxylate in the form of acetate is:

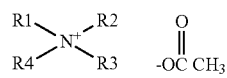

The general formula of the desensitizer as tetraalkyl ammonium hydroxide is $R_4N^+$ OH. The general structure of the desensitizer as tetraalkyl ammonium hydroxide is:

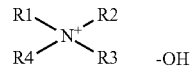

The tetraalkyl ammonium carboxylate or hydroxide desensitizers (available from Sigma Aldrich, a business having offices located in St. Louis, Mo. U.S.A.) can be selected from a variety of organic bases including, for example, tetramethyl ammonium acetate, tetramethyl ammonium hydroxide, tetraethyl ammonium acetate, tetraethyl ammonium hydroxide, tetrabutyl ammonium acetate, tetrabutyl ammonium hydroxide, trimethylbenzyl ammonium acetate, or trimethylbenzyl ammonium hydroxide. The desensitizer could also be a combination of tetraalkyl ammonium halide (fluoride, chloride, bromide or other anionic elements such as sulfate, phosphates, etc.) and alkali acetate (sodium acetate, potassium acetate, magnesium acetate, etc.) where long alkyl chain ammonium compounds may also be included. The desensitizer may also be mixtures of tetraalkyl ammonium carboxylates and/or tetraalkyl ammonium hydroxides.

Different desensitizers affect the intensity of the formed color when the printed color-changing composition is exposed to an aqueous liquid. This is shown with the following experiments. First, three samples of color-changing compositions were prepared where each sample contained tetraethyl ammonium acetate, tetramethyl ammonium acetate or tetrabutyl ammonium acetate at 10% of the total weight of the color-changing composition; all other components remained identical for each of the color-changing compositions. Each of the color-changing compositions was printed on the same substrate and allowed to substantially dry for two hours at room temperature and standard relative humidity. The dry color-changing compositions upon the substrate were wetted with an aqueous liquid. The tetraethyl ammonium acetate samples gave much higher color intensity than tetramethyl ammonium acetate or tetrabutyl ammonium acetate samples. The tetramethyl ammonium acetate sample gave a lower color intensity than the tetraethyl ammonium acetate sample and higher color intensity than the tetrabutyl ammonium acetate sample.

Second, aged samples of each of the three color-changing compositions were prepared. The color-changing compositions were printed on the same substrate as the non-aged samples and aged for five days at a constant temperature of 40° C. and constant relative humidity of 85%. The samples acclimated to room temperature before the dry color-changing compositions were wetted with an aqueous liquid. The aged tetraethyl ammonium acetate sample gave consistent higher color intensity when compared to the non-aged tetraethyl ammonium acetate sample. The aged tetraethyl ammonium acetate sample also gave the highest color intensity when compared to the aged tetramethyl ammonium acetate and tetrabutyl ammonium acetate samples. The aged tetramethyl ammonium acetate gave consistent lower color intensity when compared to the non-aged tetramethyl ammonium acetate sample. The aged tetramethyl ammonium acetate sample also gave lower color intensity when compared to the aged tetraethyl ammonium acetate sample and higher color intensity when compared to the aged tetrabutyl ammonium acetate sample. The aged tetrabutyl ammonium acetate sample gave the lowest color intensity when compared to the non-aged tetrabutyl ammonium acetate sample. The aged tetrabutyl ammonium acetate sample also gave the lowest color intensity when compared to the aged tetraethyl ammonium acetate sample and the aged tetramethyl ammonium acetate sample.

The amount of desensitizer of the disclosure can be present from about 3.0% to about 25.0% of the total weight of the color-changing composition. Desirably, the color-changing compositions of the disclosure include a desensitizer in an amount from about 10.0% to about 15.0% of the total weight of the color-changing composition.

The color-changing composition may contain a volatile organic solvent. All of the components of the color-changing composition are solubilized in one or more volatile organic solvents. Leuco dyes and the color-developer generally exhibit good solubility in organic solvents. When the mixture of the color-changing composition and an organic solvent is formed, the mixture is liquid at room temperature. The amount of solvent typically is present from about 30.0% to about 95.0% of the total weight of the color-changing composition. Desirably, the color-changing compositions of the disclosure include solvent in an amount from about 50.0% to about 80.0% of the total weight of the color-changing composition. The volatile organic solvent can be selected from low molecular weight alcohols, ethanol, methanol, propanol, isopropanol, butanol, acetone, butanone (methyl ethyl ketone), tetrahydrofuran (THF), benzene, toluene, methyl chloride, chloroform, or combinations thereof.

The color-changing composition may also contain a binder. Binders create stronger adhesion between the color-changing composition molecules and the substrate onto which the color-changing composition will be applied to. Binders provide a suitable viscosity required for printing the color-changing composition as an ink. According to the disclosure, suitable binders include, but are not limited to compositions that consist of mainly nitrocellulose, cellulose acetate propionate, cellulose acetate butyrate, and other non-water soluble binders.

The binder selection plays a role in the intensity of the formed color when the color-changing composition is wetted with an aqueous liquid. In samples of color-changing compositions formed according to the present disclosure where each sample contains a different binder in the same amount as each of the other samples, nitrocellulose and cellulose acetate propionate form higher intensity colors when compared to any of the other suitable binders. Nitrocellulose binder forms a higher intensity color than any of the other suitable binders.

A combination of binders may be used to affect the intensity of the formed color when the color-changing composition is exposed to an aqueous liquid. A combination of binders, such as cellulose acetate propionate with nitrocellulose, may also be used to control the viscosity of the color-changing composition better than if only one binder had been used in the color-changing composition. A color-changing composition of the present disclosure contained a combination of nitrocellulose and cellulose acetate propionate binders in the amount of 40% of the total weight of the color-changing composition; all other components remained identical. Each of the color-changing compositions was printed on the same substrate and allowed to substantially dry for two hours at room temperature and standard relative humidity. The dry color-changing compositions upon the substrate were wetted with an aqueous liquid. Five samples of the color-changing composition were prepared with varying amounts of each of the nitrocellulose and the cellulose acetate propionate binders. In one embodiment of the disclosure, a color-changing composition contained 8.0% nitrocellulose and 32.0% cellulose acetate propionate. The color-changing composition gave a lower intensity color upon exposure to an aqueous liquid when compared to the other embodiments. In another embodiment, a color-changing composition contained 32.0% nitrocellulose and 8.0% cellulose acetate propionate. The color-changing composition gave a higher intensity color upon exposure to an aqueous liquid when compared to the other embodiments. In a further embodiment, a color-changing composition contained 16.0% nitrocellulose and 24.0% cellulose acetate propionate. The color-changing composition gave a medium intensity color upon exposure to an aqueous liquid when compared to the other embodiments. In another embodiment, a color-changing composition contained 24.0% nitrocellulose and 16.0% cellulose acetate propionate. The color-changing composition gave a medium intensity color upon exposure to an aqueous liquid when compared to the other embodiments. In yet another embodiment, a color-changing composition contained 20.0% nitrocellulose and 20.0% cellulose acetate propionate. The color-changing composition gave a medium intensity color upon exposure to an aqueous liquid when compared to the other embodiments. Ratios of higher than 60.0% of cellulose acetate propionate against nitrocellulose demonstrate significantly decreased color intensity.

The amount of binder of the disclosure can be present from about 1.0% to about 60.0% of the total weight of the color-changing composition. Desirably, the color-changing compositions of the disclosure include binder in an amount from about 25.0% to about 40.0% of the total weight of the color-changing composition.

An embodiment of the color-changing composition of the present disclosure is a color-changing composition that includes a leuco dye or combinations of leuco dyes in the amount of 5.0% of the total weight of the color-changing composition, a color-developer or combination of color-developers in the amount of 8.0% of the total weight of the color-changing composition, a desensitizer or combination of desensitizers in the amount of 14.0% of the total weight of the color-changing composition, a binder or combination of binders in the amount of 25.0% of the total weight of the color-changing composition, and a volatile organic solvent or combination of volatile organic solvents making up the remainder of the color-changing composition.

The color-changing compositions of the disclosure may be applied to a substrate and have a colorless or largely colorless state of appearance (i.e., either no color or very weak background shade). The volatile organic solvent evaporates after application of the color-changing composition to the substrate. When in the form of a film layer on a substrate, the color-changing compositions of the disclosure are wettable but insoluble in water. This feature makes the color-changing compositions desirable for use in articles where the color-changing compositions will be exposed to wetness, such as for example, components of disposable, absorbent articles. The feature also results in color-changing compositions that are durable and that are resistant to leaching out of the film-like printed layer. The printed layer may be formed on the substrate in a desired pattern including stripes, dots, geometric shapes and irregular shapes and combinations of such pattern elements. The printed layer may also be formed on the substrate as an alpha-numeric character, an anthropomorphic image, a pictorial representation of an animal, a pictorial representation of an inanimate object, a cartoon character, a product or company logo and a trademark or brand or combinations of such pictorial elements. The color-changing compositions may be printed as a thin film or applied as a heavier coating upon the substrate.

The present disclosure is also directed to a color-changing material that includes a substrate and a printed layer. This color-changing material may function as a wetness indicator. The substrate may be in the form of a porous foam, a reticulated foam, cellulose tissues, a plastic film, a woven material, or a nonwoven material. Suitable plastic films that may be used to form the substrate include polyethylene films and polypropylene films, including porous or breathable films embedded with calcium carbonate. Suitable woven materials include woven materials made from natural fibers, synthetic fibers or combinations of natural and synthetic fibers. Natural fibers include cotton, silk, and wool fibers and synthetic fibers include polyester, polyethylene, and polypropylene fibers. Suitable nonwoven materials include nonwoven materials made through traditional techniques such as spunbond, meltblown, and bonded carded web materials. The spunbond, meltblown, and bonded carded web materials may be made from suitable synthetic fibers such as polyester, polyethylene, and polypropylene fibers. The substrate may include combinations of the materials identified above such as a substrate that includes both a porous foam and a nonwoven material or a substrate that includes both a plastic film and a nonwoven material. More specifically, the nonwoven substrate may be a spunbond or other nonwoven material that is used to form the outer cover, that is, the backsheet, of a disposable diaper.

The color-changing materials of the disclosure include a printed layer that is adhered to the substrate. The printed layer may be formed by the color-changing composition itself or the color-changing composition may be applied to or incorporated into the printed layer. In an embodiment, the color-changing composition may be printed directly upon the substrate surface. In another embodiment, a varnish or other coating may first be applied by printing on to the substrate surface. The color-changing composition may then be applied by printing upon the varnish or other coating that was first applied to the substrate surface.

Because the color-changing compositions of the disclosure are liquid at room temperature, the compositions can be applied through printing or stamping either directly onto the substrate (thereby self-forming the printed layer) or onto a pre-existing layer having a film-like structure and associated with the substrate, such as a coating. The color-changing compositions can be applied using such printing methods as flexographic printing, gravure printing or any suitable printing method for the given substrate.

Because the outer cover of an absorbent article, such as a disposable diaper, is typically adjacent to the absorbent core of the article, it may be desirable to apply the color-changing composition to a component of the absorbent article that is adjacent to the absorbent core. Adjacent as used herein can mean components in direct contact to each other or having other structure(s) between the components. In an embodiment, adhesive may be between the absorbent core and the outer cover. In another embodiment, the absorbent core may be wrapped with a nonwoven material to assist in containing the cellulose fiber and/or superabsorbent materials. The core wrapping material and adhesive may be between the absorbent core and the outer cover. By using this arrangement, the color-changing composition can come in direct contact with an aqueous liquid, such as urine or runny fecal matter, and it can be used to indicate a change in condition of the absorbent core, such as wetness.

The color-changing composition is applied to the substrate through printing, as an ink, in a colorless or largely colorless state. The color-changing composition in the form of ink upon the substrate will remain colorless or largely colorless even at the high relative humidity conditions described herein.

In another embodiment of the disclosure, the color-changing composition may include water. For example, the color-changing compositions of the present disclosure have been formulated to simulate the effects of moisture condensing into the ink composition with a maximum amount of water to 5% of the total weight of the color-changing composition. The color-changing compositions containing water demonstrate a slight color appearance when initially coated or printed onto a substrate. The color-changing compositions containing water are colorless or largely colorless after substantial drying upon the substrate. The substrates printed with the color-changing compositions formulated with water were allowed to substantially dry at room temperature. Samples of these substrates were then aged in a chamber held at a temperature of 40° C. and a constant relative humidity of 85% for up to ten weeks. The aged and non-aged samples of the substrates having the color-changing composition printed thereon were wetted with an aqueous liquid at room temperature. Color appeared immediately or within seconds depending on the concentration of the color-changing component in the color-changing composition and the volume of the urine or aqueous liquid insult. The color intensity is consistent among the aged and non-aged samples. These results confirm that the color-changing composition of the present disclosure that has had water condense into the composition or that has been exposed to high relative humidity conditions does not lose efficacy when printed on substrates and remains colorless or largely colorless until wetted with an aqueous liquid.

Figure 1B:
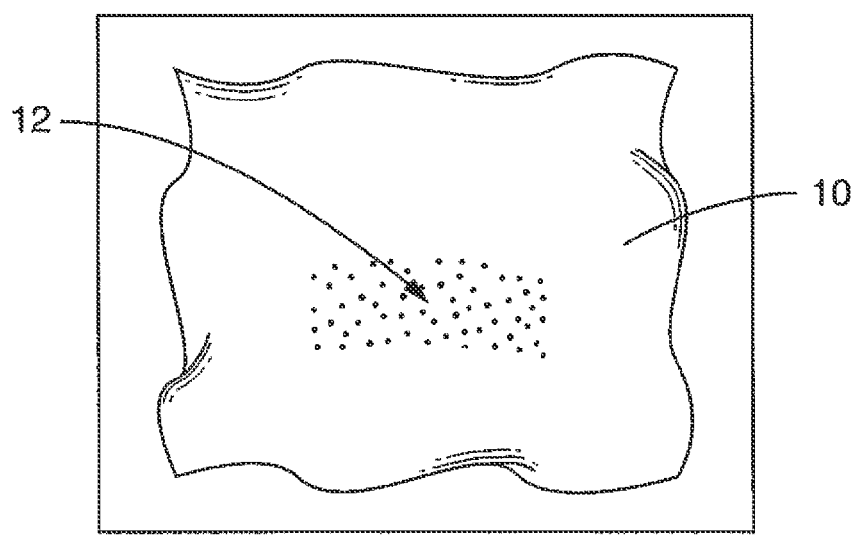
FIG. 1B shows the development of color on the substrate of FIG. 1A after an aqueous liquid has reacted with the ink composition.

FIGS. 1A-1B are illustrations that show a substrate surface 10 that has been printed with the color-changing composition 12 according to the present disclosure. FIG. 1A shows the substrate surface 10 and a color-changing composition 12 at an initial stage with a colorless appearance. FIG. 1B shows the same substrate surface 10 and almost immediately after the color-changing composition 12 is wetted with an aqueous liquid.

In an embodiment, a color-changing composition of the present disclosure may be printed upon a nonwoven substrate. The substrate may be a portion of the outer cover of a disposable, absorbent article, the outer cover of the disposable, absorbent article or any other component of the disposable, absorbent article that is adjacent to the absorbent core.

The color-changing composition of the present disclosure is useful for application to disposable absorbent articles such as pants, diapers and pads. An absorbent article of the present disclosure includes an absorbent core, and optionally includes a topsheet and/or a backsheet. The absorbent core may be disposed between the topsheet and the backsheet. To gain a better understanding of the structure, attention is directed to FIGS. 2 and 3 showing an exemplary training pant and a wetness indicator of the present disclosure.

Figure 2:
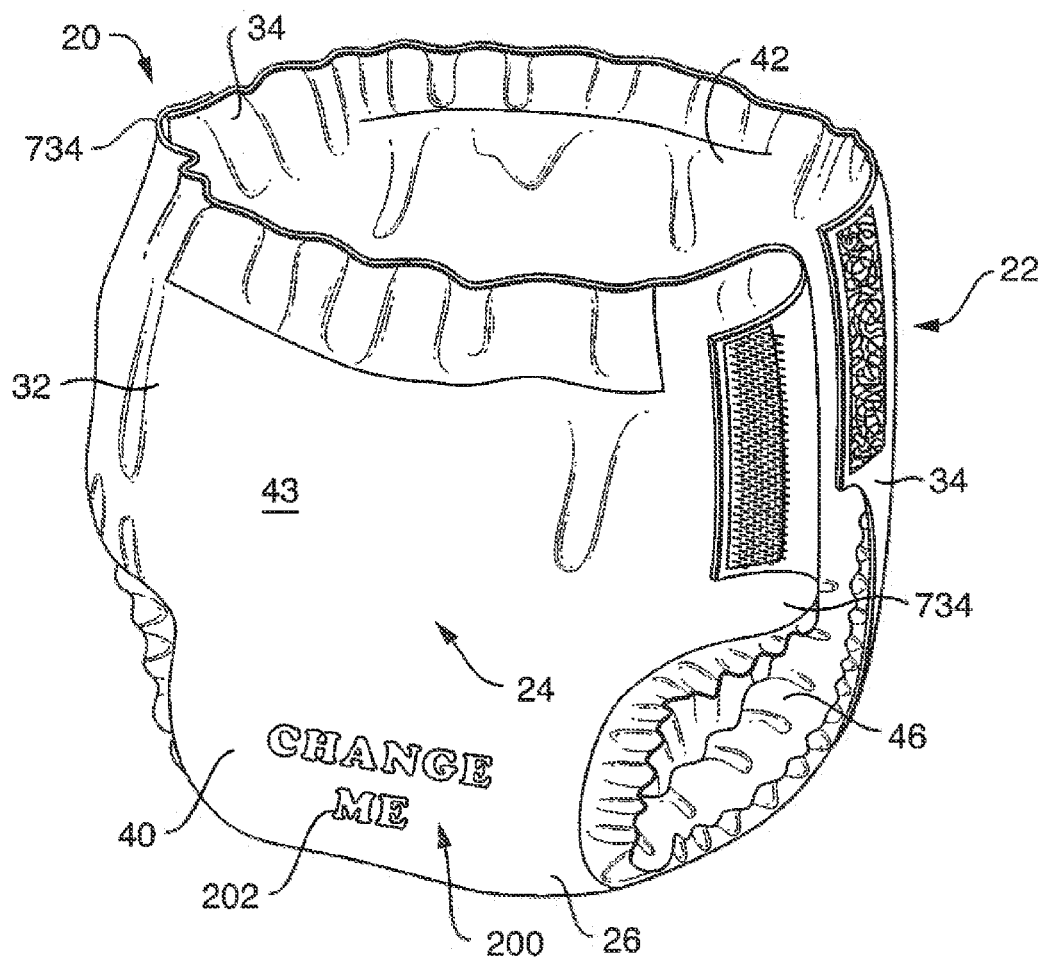
FIG. 2 is a front perspective view of one embodiment of an absorbent article.
Figure 3:
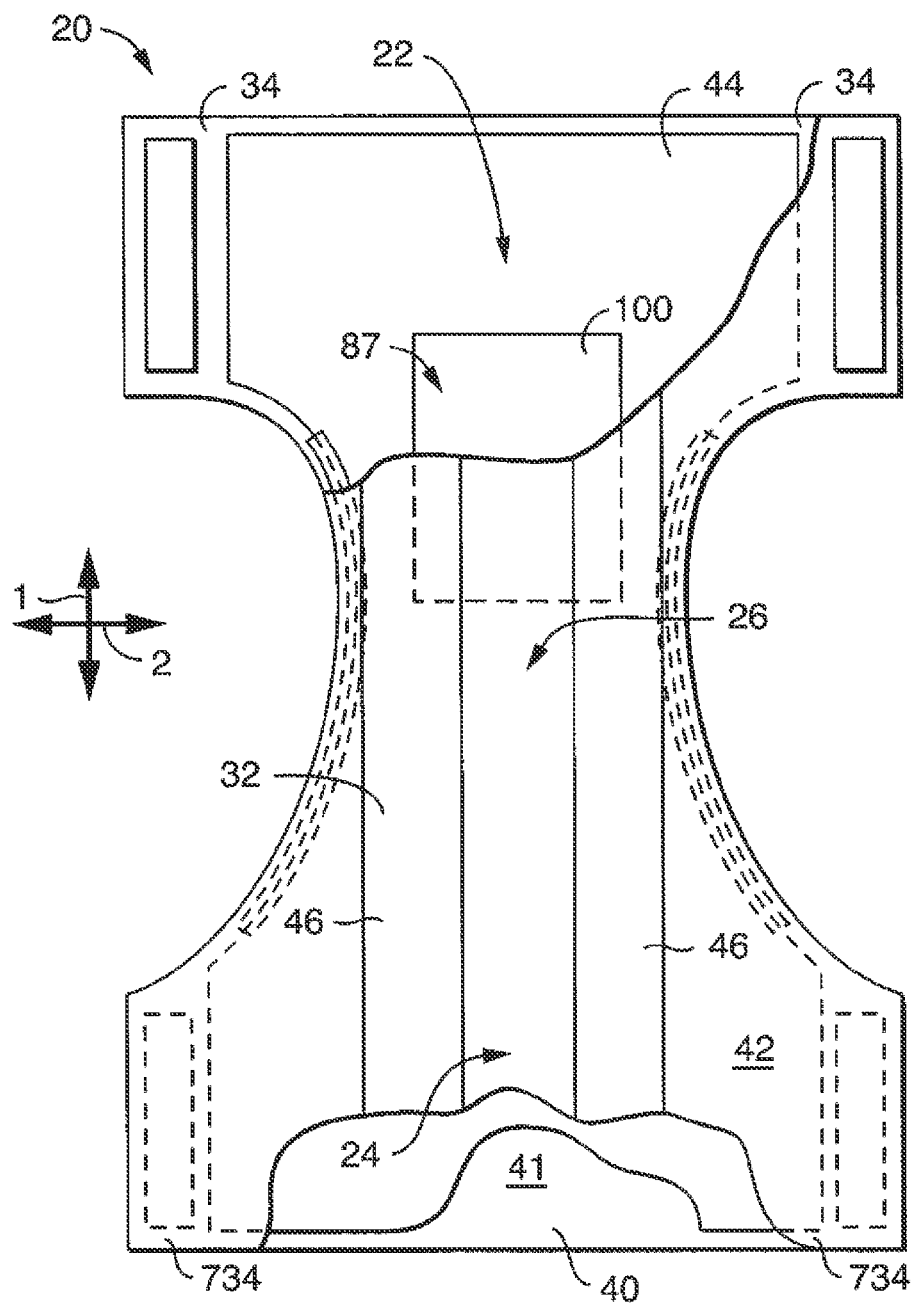
FIG. 3 is a plan view of the absorbent article of FIG. 2, in an unfastened, unfolded, and laid out flat configuration.

FIG. 2 illustrates a training pant 20 in a partially fastened condition, and FIG. 3 illustrates a training pant 20 in an opened and unfolded state. The training pant 20 defines a longitudinal direction 1 that extends from the front of the training pant 20 when worn to the back of the training pant 20. Perpendicular to the longitudinal direction 1 is a lateral direction 2.

The training pant 20 defines a front region 22, a back region 24, and a crotch region 26 extending longitudinally between and interconnecting the front and back regions 22, 24. The pant 20 also defines an inner surface (i.e., body-facing surface) adapted in use (e.g., positioned relative to the other components of the pant) to be disposed toward the wearer, and an outer surface (i.e., garment-facing surface) opposite the inner surface. The training pant 20 has a pair of laterally opposite side edges and a pair of longitudinally opposite waist edges.

The illustrated pant 20 may include a chassis 32, a pair of laterally opposite front side panels 34 extending laterally outward at the front region 22 and a pair of laterally opposite back side panels 734 extending laterally outward at the back region 24.

The pant 20 further includes a wetness indicator 100 that is made from a substrate having the color-changing composition disposed on the substrate surface 87. The wetness indicator 100 is placed, for example, between the absorbent core 44 and the topsheet 42 so that the wetness indicator 100 substrate surface 87 is revealed from the inside of the pant 20. In an alternative embodiment (not shown), the wetness indicator 100 is located between the backsheet 40 and the absorbent core 44 so that the wetness indicator 100 substrate surface 87 may be viewed through the garment-facing surface 43 of the backsheet 40. Wetness indicator 100 may be located anywhere on the training pant 20 where wetness sensing is desired.

In another embodiment, a wetness indicator 200 is made by printing the color-changing composition onto the body-facing surface 41 of the backsheet 40 to form indicia 202. Indicia 202 may be any design(s), letter(s), number(s), or combinations thereof. When the absorbent core 44 is wetted with enough urine or other aqueous liquid to make contact with the wetness indicator 200, the indicia 202 develops color to communicate the message or signal that is visible from the garment-facing surface 43 of backsheet 40, indicating that the training pant 20 is soiled. For example, indicia 202 could form a message or signal such as CHANGE ME.

The chassis 32 includes a backsheet 40 and a topsheet 42 that may be joined to the backsheet 40 in a superimposed relation therewith by adhesives, ultrasonic bonds, thermal bonds or other conventional techniques. The chassis 32 may further include an absorbent core 44, such as shown in FIG. 3, disposed between the backsheet 40 and the topsheet 42 for absorbing fluid body exudates exuded by the wearer, and may further include a pair of containment flaps 46 secured to the topsheet 42 or the absorbent core 44 for inhibiting the lateral flow of body exudates.

The backsheet, or outer cover, 40 may be constructed of a nonwoven material. The backsheet 40, may be a single layer of a fluid impermeable material, or alternatively may be a multi-layered laminate structure in which at least one of the layers is fluid impermeable.

Examples of suitable backsheet 40 materials are spunbond-meltblown fabrics, spunbond-meltblown-spunbond fabrics, spunbond fabrics, or laminates of such fabrics with films, or other nonwoven webs; elastomeric materials that may include cast or blown films, meltblown fabrics or spunbond fabrics composed of polyethylene, polypropylene, or polyolefin elastomers, as well as combinations thereof. The backsheet 40 may include materials that have elastomeric properties through a mechanical process, printing process, heating process or chemical treatment. For example, such materials may be apertured, creped, neck-stretched, heat activated, embossed, and micro-strained, and may be in the form of films, webs, and laminates.

The topsheet 42 is suitably compliant, soft-feeling and non-irritating to the wearer's skin. The topsheet 42 is also sufficiently liquid permeable to permit liquid body exudates to readily penetrate through its thickness to the absorbent core 44. A suitable topsheet 42 may be manufactured from a wide selection of web materials, such as porous foams, reticulated foams, apertured plastic films, woven and non-woven webs, or a combination of any such materials. For example, the topsheet 42 may include a meltblown web, a spunbonded web, or a bonded-carded-web composed of natural fibers, synthetic fibers or combinations thereof. The topsheet 42 may be composed of a substantially hydrophobic material, and the hydrophobic material may optionally be treated with a surfactant or otherwise processed to impart a desired level of wettability and hydrophilicity.

The topsheet 42 may also be extensible and/or elastomerically extensible. Suitable elastomeric materials for construction of the topsheet 42 can include elastic strands, LYCRA elastics, cast or blown elastic films, nonwoven elastic webs, meltblown or spunbond elastomeric fibrous webs, as well as combinations thereof. Examples of suitable elastomeric materials include KRATON elastomers, HYTREL elastomers, ESTANE elastomeric polyurethanes (available from Noveon, a business having offices located in Cleveland, Ohio U.S.A.), or PEBAX elastomers. The topsheet 42 can also be made from biaxially stretchable materials as described in U.S. Pat. No. 6,969,378 to Vukos et al. which is incorporated herein by reference in a manner that is consistent herewith.

The training pant 20 can optionally further include a surge management layer which may be located adjacent the absorbent core 44 and attached to various components in the training pant 20 such as the absorbent core 44 or the topsheet 42 by methods known in the art, such as by using an adhesive. Examples of suitable surge management layers are described in U.S. Pat. No. 5,486,166 to Bishop et al.; U.S. Pat. No. 5,490,846 to Ellis et al.; and U.S. Pat. No. 5,820,973 to Dodge et al., each of which is incorporated herein by reference in a manner that is consistent herewith.

The training pant 20 can further comprise an absorbent core 44. The absorbent core 44 may have any of a number of shapes. The absorbent core 44 can be attached in an training pant 20, such as to the backsheet 40 and/or the topsheet 42 for example, by bonding means known in the art, such as ultrasonic, pressure, adhesive, aperturing, heat, sewing thread or strand, autogenous or self-adhering, hook-and-loop, or any combination thereof.

The absorbent core 44 can be formed using methods known in the art. While not being limited to the specific method of manufacture, the absorbent core 44 can utilize forming drum systems, for example, see U.S. Pat. No. 4,666,647 to Enloe et al., U.S. Pat. No. 4,761,258 to Enloe, U.S. Pat. No. 6,630,088 to Venturino et al., and U.S. Pat. No. 6,330,735 to Hahn et al., each of which is incorporated herein by reference in a manner that is consistent herewith. Examples of techniques which can introduce a selected quantity of optional superabsorbent particles into a forming chamber are described in U.S. Pat. No. 4,927,582 to Bryson and U.S. Pat. No. 6,416,697 to Venturino et al., each of which is incorporated herein by reference in a manner that is consistent herewith.

In some desirable aspects, the absorbent core 44 includes cellulose fiber and/or synthetic fiber, such as meltblown fiber, for example. Thus, in some aspects, a meltblown process can be utilized, such as to form the absorbent core 44 in a coform line. In some aspects, the absorbent core 44 can have a significant amount of stretchability.

The absorbent core 44 can additionally or alternatively include absorbent and/or superabsorbent material. Accordingly, the absorbent core 44 can comprise a quantity of superabsorbent material and optionally cellulose fiber or fluff contained within a matrix of fibers. It should be understood that the absorbent core 44 is not restricted to use with superabsorbent material and optionally cellulose fluff. In some aspects, the absorbent core 44 may additionally include materials such as surfactants, ion exchange resin particles, moisturizers, emollients, perfumes, fluid modifiers, odor control additives, and the like, and combinations thereof. In addition, the absorbent core 44 can include foam. Further, the absorbent core 44 may be wrapped with a material that assists in maintaining the integrity of the absorbent core 44 such that the material contains the superabsorbent material and the optionally cellulose fiber while allowing urine or aqueous liquid to pass through the absorbent core 44. Suitable core wrap materials may be selected from cellulose tissue, nonwoven material such as spunbond or meltblown webs, and apertured film.

Various materials and methods for constructing training pants are disclosed in U.S. Pat. No. 6,761,711 to Fletcher et al.; U.S. Pat. No. 4,940,464 to Van Compel et al.; U.S. Pat. No. 5,766,389 to Brandon et al., and U.S. Pat. No. 6,645,190 to Olson et al., each of which is incorporated herein by reference in a manner that is consistent herewith.

The following are various examples that illustrate aspects of the present disclosure:

Exemplary Color-Changing Composition and Color-Changing Material #1:

Three exemplary samples of color-changing compositions of the present disclosure were prepared, each sample having a different leuco dye component. The samples included a desensitizer of tetraethyl ammonium acetate, $Et_4N^+$ OAc, in the amount of 10.0% of the total weight of the color-changing composition, a color-developer of zinc salicylate in an amount of 8.0% of the total weight of the color-changing composition, a binder of nitrocellulose in the amount of 20.0% of the total weight of the color-changing composition, a leuco dye in the amount of 6.0% of the total weight of the color-changing composition, and an organic solvent of butanone in the amount of 56.0% of the total weight of the color-changing composition. Each of the three samples contained a different leuco dye: 3,3-bis(1-n-butyl-2-methyl-3-indolyl)phthalide (Red 40), 3,3-bis(4-diethylphenyl)-4-azaphthalide (GN-2) and 3-(4-diethylamino-2-ethoxyphenyl)-3-(1-ethyl-2-methyl-3-indolyl)-4-azaphthalide (Blue 63). Each sample of the color-changing composition was fully mixed by vortex for 5 minutes until a colorless solution was formed.

A color-changing material was prepared by coating an amount of each sample of the color-changing composition on a breathable film material of polyethylene (such as would be used to form the outer cover of a disposable absorbent article) by using different sized anilox rollers to form a thin coating on the film. Anilox rollers of 9.2 cell volume and 27.4 cell volume were used for each of the three color-changing compositions prepared as described above for a total of six samples. The color-changing composition was allowed to dry under ambient conditions for two hours. Each of the six dried samples was wetted with an aqueous liquid. Each of the dried samples rapidly formed the colors of red, green and blue, respectively.

Additional color-changing materials were prepared in the manner described above for each of the color-changing composition samples. The color-changing material samples were placed in an aging chamber having a constant temperature of 40° C. and a constant relative humidity of 85%. The samples remained in the aging chamber for five days. The color-changing compositions on the color-changing materials remained colorless upon removal from the aging chamber. The samples acclimated to standard room temperature and standard relative humidity. Each of the aged samples was wetted with an aqueous liquid. Each of the aged samples rapidly formed the colors of red, green and blue. Upon comparison between the aged and non-aged samples, each color maintained substantially consistent color intensity.

Exemplary Color-Changing Composition and Color-Changing Material #2:

Three exemplary samples of color-changing compositions of the present disclosure were prepared, each having a different leuco dye component. The samples included a desensitizer of tetramethyl ammonium acetate, $Me_4N^+$ OAc, in the amount of 10.0% of the total weight of the color-changing composition, a color-developer of zinc salicylate in an amount of 8.0% of the total weight of the color-changing composition, a binder of nitrocellulose in the amount of 20.0% of the total weight of the color-changing composition, a leuco dye in the amount of 6.0% of the total weight of the color-changing composition and an organic solvent of butanone in the amount of 56.0% of the total weight of the color-changing composition. Each of the three samples contained a different leuco dye: 3,3-bis(1-n-butyl-2-methyl-3-indolyl)phthalide (Red 40), 3,3-bis(4-diethylphenyl)-4-azaphthalide (GN-2) and 3-(4-diethylamino-2-ethoxyphenyl)-3-(1-ethyl-2-methyl-3-indolyl)-4-azaphthalide (Blue 63). Each sample of the color-changing composition was fully mixed by vortex for 5 minutes until colorless solution was formed.

A color-changing material was prepared by coating an amount of each sample of the color-changing composition on a breathable film material of polyethylene (such as would be used to form the outer cover of a disposable absorbent article) by using different sized anilox rollers to form a thin coating on the film. Anilox rollers of 9.2 cell volume and 27.4 cell volume were used for each of the three color-changing compositions prepared as described above for a total of six samples. The color-changing composition was allowed to dry under ambient conditions for two hours. Each of the six dried samples was wetted with an aqueous liquid. Each of the dried samples rapidly formed the colors of red, green and blue, respectively.

Additional color-changing materials were prepared in the manner described above for each of the color-changing composition samples. The color-changing material samples were placed in an aging chamber having a constant temperature of 40° C. and a constant relative humidity of 85%. The samples remained in the aging chamber for five days. The color-changing compositions on the color-changing materials remained colorless upon removal from the aging chamber. The samples acclimated to standard room temperature and standard relative humidity. Each of the aged samples was wetted with an aqueous liquid. Each of the aged samples rapidly formed the colors of red, green and blue. Upon comparison between the aged and non-aged samples, each color maintained substantially consistent color intensity.

Exemplary Color-Changing Composition and Color-Changing Material #3:

Three exemplary samples of color-changing compositions of the present disclosure were prepared, each sample having a different leuco dye component. The samples included a desensitizer of tetrabutyl ammonium acetate, $Bu_4N^+$ OAc, in the amount of 10.0% of the total weight of the color-changing composition, a color-developer of zinc salicylate in an amount of 8.0% of the total weight of the color-changing composition, a binder of nitrocellulose in the amount of 20.0% of the total weight of the color-changing composition, a leuco dye in the amount of 6.0% of the total weight of the color-changing composition and an organic solvent of butanone in the amount of 56.0% of the total weight of the color-changing composition. Each of the three samples contained a different leuco dye: 3,3-bis(1-n-butyl-2-methyl-3-indolyl)phthalide (Red 40), 3,3-bis(4-diethylphenyl)-4-azaphthalide (GN-2) and 3-(4-diethylamino-2-ethoxyphenyl)-3-(1-ethyl-2-methyl-3-indolyl)-4-azaphthalide (Blue 63). Each sample of the color-changing composition was fully mixed by vortex for 5 minutes until colorless solution was formed.

A color-changing material was prepared by coating an amount of each sample of the color-changing composition on a breathable film material of polyethylene (such as would be used to form the outer cover of a disposable absorbent article) by using different sized anilox rollers to form a thin coating on the film. Anilox rollers of 9.2 cell volume and 27.4 cell volume were used for each of the three color-changing compositions prepared as described above for a total of six samples. The color-changing composition was allowed to dry under ambient conditions for two hours. Each of the six dried samples was wetted with an aqueous liquid. Each of the dried samples rapidly formed the colors of red, green and blue, respectively. Upon comparison of samples from Exemplary Color-Changing Composition and Color-Changing Material #1 ($Et_4N^+$ OAc) and #2 ($Me_4N^+$ OAc), the intensity of the samples formed with $Bu_4N^+$ OAc exhibited a lower color intensity.

Additional color-changing materials were prepared in the manner described above for each of the color-changing composition samples. The color-changing material samples were placed in an aging chamber having a constant temperature of 40° C. and a constant relative humidity of 85%. The samples remained in the aging chamber for five days. The color-changing compositions on the color-changing materials remained colorless upon removal from the aging chamber. The samples acclimated to standard room temperature and standard relative humidity. Each of the aged samples was wetted with an aqueous liquid. Each of the aged samples rapidly formed the colors of red, green and blue. Upon comparison between the aged and non-aged samples, each of the aged samples exhibited lower color intensity. Upon comparison of aged samples from Exemplary Color-Changing Composition and Color-Changing Material #1 ($Et_4N^+$ OAc) and #2 ($Me_4N^+$ OAc), the intensity of the aged samples formed with $Bu_4N^+$ OAc exhibited a lower color intensity.

Exemplary Color-Changing Composition and Color-Changing Material #4:

Five exemplary samples of color-changing compositions of the present disclosure were prepared, each sample having a different binder component. The samples included a desensitizer of tetraethyl ammonium acetate, $Et_4N^+$ OAc, in the amount of 5.5% of the total weight of the color-changing composition, a color-developer of 4,4-dihydroxybenzophenone in an amount of 4.0% of the total weight of the color-changing composition, a leuco dye, 3,3-bis(1-n-butyl-2-methyl-3-indolyl)phthalide (Red 40), in the amount of 5.0% of the total weight of the color-changing composition, a binder in the amount of 20.0% of the total weight of the color-changing composition and an organic solvent of butanone in the amount of 65.5% of the total weight of the color-changing composition. Each of the five samples contained a different binder: nitrocellulose, cellulose acetate propionate, cellulose acetate butyrate, polyvinyl butyral or ethyl cellulose. Each sample of the color-changing composition was fully mixed by vortex for 5 minutes until a colorless solution was formed.

A color-changing material was prepared by coating an amount of each sample of the color-changing composition on a breathable film material of polyethylene (such as would be used to form the outer cover of a disposable absorbent article) by using different sized anilox rollers to form a thin coating on the film. Anilox rollers of 9.2 cell volume and 27.4 cell volume were used for each of the five color-changing compositions prepared as described above for a total of ten samples. The color-changing composition was allowed to dry under ambient conditions for two hours. Each of the ten dried samples was wetted with an aqueous liquid. Each of the dried samples rapidly formed the color red in various intensities. The red color of the samples formed with cellulose acetate propionate and nitrocellulose had higher color intensity than samples formed with cellulose acetate butyrate, polyvinyl butyral or ethyl cellulose.

Exemplary Color-Changing Composition and Color-Changing Material #5:

Four exemplary samples of color-changing compositions of the present disclosure were prepared with each having a different binder mixture. Each sample includes a desensitizer of tetraethyl ammonium acetate, $Et_4N^+$ OAc, in the amount of 5.5% of the total weight of the color-changing composition, a color-developer of 4,4-dihydroxybenzophenone in an amount of 4.0% of the total weight of the color-changing composition, a leuco dye, 3,3-bis(1-n-butyl-2-methyl-3-indolyl)phthalide (Red 40), in the amount of 5.0% of the total weight of the color-changing composition, a binder in the amount of 20.0% of the total weight of the color-changing composition and an organic solvent of butanone in the amount of 65.5% of the total weight of the color-changing composition. Each of the four samples contained a binder combination containing different amounts of nitrocellulose and cellulose acetate. Each sample of the color-changing composition was fully mixed by vortex for 5 minutes until a colorless solution was formed. The different binder combinations are shown in Table 1.

A color-changing material was prepared by coating an amount of each sample of the color-changing composition on a breathable film material of polyethylene (such as would be used to form the outer cover of a disposable absorbent article) by using different sized anilox rollers to form a thin coating on the film. Anilox rollers of 9.2 cell volume and 27.4 cell volume were used for each of the four color-changing compositions prepared as described above for a total of eight samples. The color-changing composition was allowed to dry under ambient conditions for two hours. Each of the eight dried samples was wetted with an aqueous liquid. Each of the dried samples rapidly formed the color of red in various levels of intensity. The intensity of each sample of the red color produced is shown in Table 1.

TABLE 1

| Sample | Nitrocellulose (%) | Cellulose Acetate Propionate (%) | Intensity |
|---|---|---|---|
| 1 | 8 | 32 | Low |
| 2 | 16 | 24 | Medium |
| 3 | 24 | 16 | Medium |
| 4 | 20 | 20 | Medium |
| 5 | 32 | 8 | High |

Exemplary Color-Changing Composition and Color-Changing Material #6:

Three exemplary samples of color-changing compositions of the present disclosure were prepared, each having different water content. The color-changing compositions of the present disclosure were formulated with a maximum amount of water to 5% of the total weight of the color-changing composition. These samples were prepared to simulate the effects of moisture condensing onto the color-changing compositions when printed on a substrate due to high relative humidity conditions. Each sample includes a desensitizer of tetraethyl ammonium acetate, $Et_4N^+$ OAc, in the amount of 9.5% of the total weight of the color-changing composition, a color-developer of zinc salicylate in an amount of 8.5% of the total weight of the color-changing composition, a leuco dye, 3-(4-diethylamino-2-ethoxyphenyl)-3-(1-ethyl-2-methyl-3-indolyl)-4-azaphthalide (Blue 63), in the amount of 5.0% of the total weight of the color-changing composition, cellulose acetate propionate in the amount of 20.0% of the total weight of the color-changing composition and an organic solvent of methyl ethyl ketone in the amount of 57.0% of the total weight of the color-changing composition. Water was added to each of the three samples in the amounts of 1.0%, 2.0% and 5.0% of the total weight of the color-changing compositions. An additional sample of the color-changing composition was prepared that did not contain water, that is, 0% of the total weight of the color-changing composition. Each sample of the color-changing composition was fully mixed by vortex for 5 minutes until colorless solution was formed.

A color-changing material was prepared by coating an amount of each sample of the color-changing composition on a breathable film material of polyethylene (such as would be used to form the outer cover of a disposable absorbent article) by using different sized anilox rollers to form a thin coating on the film. Anilox rollers of 9.2 cell volume and 27.4 cell volume were used for each of the four color-changing compositions prepared as described above for a total of eight samples. The water-containing color-changing composition samples indicated a slight appearance of color in the color-changing composition immediately after the composition was rolled onto the polyethylene film. The rolled coating was allowed to dry under ambient conditions for two hours. The color-changing composition was colorless when fully dry. Each of the eight dried samples was wetted with an aqueous liquid. Each of the dried samples rapidly formed the color blue of similar intensity.

Additional color-changing materials were prepared in the manner described above for each of the eight color-changing composition samples. The eight color-changing material samples were placed in an aging chamber having a constant temperature of 40° C. and a constant relative humidity of 85%. The samples remained in the aging chamber for five days. The color-changing compositions on the color-changing materials remained colorless upon removal from the aging chamber. The samples acclimated to standard room temperature and standard relative humidity. Each of the eight aged samples was wetted with an aqueous liquid. Each of the aged samples rapidly formed the color blue of similar intensity. Results are summarized in Table 2.

TABLE 2

| Sample | Water (%) | Anilox Roller Cell Volume | Color-Non-aged | Color-Aged |
|---|---|---|---|---|
| 1 | 0 | 9.2 | Blue | Blue |
| 2 | 0 | 27.4 | Blue | Blue |
| 3 | 1 | 9.2 | Blue | Blue |
| 4 | 1 | 27.4 | Blue | Blue |
| 5 | 2 | 9.2 | Blue | Blue |
| 6 | 2 | 27.4 | Blue | Blue |
| 7 | 5 | 9.2 | Blue | Blue |
| 8 | 5 | 27.4 | Blue | Blue |

Exemplary Color-Changing Composition and Color-Changing Material #7:

An exemplary sample of the color-changing composition of the present disclosure was prepared to simulate shelf life of a consumer product when exposed to high relative humidity conditions. The sample included a desensitizer of tetraethyl ammonium acetate, $Et_4N^+$ OAc, in the amount of 8.0% of the total weight of the color-changing composition, a color-developer of zinc salicylate in an amount of 6.0% of the total weight of the color-changing composition, a leuco dye, 3,3-bis(4-diethylphenyl)-4-azaphthalide (GN2) in the amount of 5.0% of the total weight of the color-changing composition, nitrocellulose in the amount of 10.0% of the total weight of the color-changing composition, cellulose acetate propionate in the amount of 15.0% of the total weight of the color-changing composition, an organic solvent of methyl ethyl ketone in the amount of 30 ml and an organic solvent of ethanol in the amount of 10 ml. The sample of the color-changing composition was fully mixed by vortex for 5 minutes until colorless solution was formed.

A color-changing material was prepared by coating an amount of the color-changing composition on a breathable film material of polyethylene (such as would be used to form the outer cover of a disposable absorbent article) by using a 9.2 cell volume anilox roller to form a thin coating on the polyethylene film. The rolled coating was allowed to dry under ambient conditions for two hours. The color-changing composition was colorless when fully dry. The dried sample was wetted with an aqueous liquid which caused the sample to rapidly form the color green.

The color-changing material was also placed in an aging chamber having a constant temperature of 40° C. and a constant relative humidity of 85%. The color-changing material remained in the aging chamber for up to ten weeks. The color-changing compositions on the color-changing material remained colorless upon removal from the aging chamber. The samples acclimated to standard room temperature and standard relative humidity. The aged sample was wetted with an aqueous liquid which caused the sample to rapidly form the color green of similar intensity whether the sample was aged for 1 week, 2 weeks, 8 weeks, 10 weeks, or non-aged.

Exemplary Color-Changing Composition and Color-Changing Material #8:

An exemplary sample of the color-changing composition of the present disclosure was prepared to simulate shelf life of a consumer product when exposed to high relative humidity conditions. The sample includes an organic solvent of methyl ethyl ketone in the amount of 1 ml, a leuco dye, 3,3-bis(1-n-butyl-2-methyl-3-indolyl)phthalide (Red 40) in the amount of 20 mg (2.0%), a color-developer of 4,4'-dihydroxybenzophenone in an amount of 150 mg (15.0%) and cellulose acetate butyrate in the amount of 250 mg (25%) to create the developed dye solution. A desensitizer, tetraethyl ammonium chloride, $Et_4N^+$ Cl, in the amount of 18 mg was dissolved into 50 µl of ethanol. The ethanol solution was mixed with 100 µl of the developed dye solution (1 minute). The mixed solution of the color-changing composition immediately became colorless.

A color-changing material was prepared by coating an amount of the color-changing composition on a breathable film material of polyethylene (such as would be used to form the outer cover of a disposable absorbent article) by using a 27.4 cell volume anilox roller to form a thin coating on the polyethylene film. The rolled coating was allowed to dry under ambient conditions for two hours. The sample was wetted with an aqueous liquid which caused the sample to rapidly form the color red.

The color-changing sample was also placed in an aging chamber having a constant temperature of 40° C. and a constant relative humidity of 85%. The sample remained in the aging chamber for forty days. The color-changing composition on the color-changing material remained colorless upon removal from the aging chamber. The samples acclimated to standard room temperature and standard relative humidity. The sample was wetted with an aqueous liquid which caused the sample to rapidly form the color red of similar intensity when compared to the non-aged sample.

In the interests of brevity and conciseness, any ranges of values set forth in this disclosure contemplate all values within the range and are to be construed as support for claims reciting any sub-ranges having endpoints which are whole number values within the specified range in question. By way of hypothetical example, a disclosure of a range from 1 to 5 shall be considered to support claims to any of the following ranges: 1 to 5; 1 to 4; 1 to 3; 1 to 2; 2 to 5; 2 to 4; 2 to 3; 3 to 5; 3 to 4; and 4 to 5.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description are, in relevant part, incorporated herein by reference; the citation of any document is not to be construed as an admission that it is prior art with respect to the present disclosure. To the extent that any meaning or definition of a term in this written document conflicts with any meaning or definition of the term in a document incorporated by references, the meaning or definition assigned to the term in this written document shall govern.

While particular embodiments have been illustrated and described, it would be obvious to those skilled in the art that various other changes and modifications can be made without departing from the spirit and scope of this disclosure. It is therefore intended to cover in the appended claims all such changes and modifications that are within the scope of this disclosure.

We claim:

1. A color-changing composition comprising:
    a leuco dye;
    a color-developer;
    a desensitizer;
    a binder; and
    an organic solvent;
    wherein the desensitizer is selected from the group consisting of a tetraalkyl ammonium carboxylate, tetraalkyl ammonium hydroxide, tetraalkyl ammonium halide and combinations thereof.

2. The color-changing composition of claim 1 wherein the leuco dye is 0.1% to 20.0% of the total weight of the color-changing composition.

3. The color-changing composition of claim 1 wherein the color-developer is 0.1% to 17.0% of the total weight of the color-changing composition.

4. The color-changing composition of claim 1 wherein the desensitizer is 3.0% to 25.0% of the total weight of the color-changing composition.

5. The color-changing composition of claim 1 wherein the desensitizer is 10.0% to 15.0% of the total weight of the color-changing composition.

6. The color-changing composition of claim 1 wherein the binder is 1.0% to 60.0% of the total weight of the color-changing composition.

7. The color-changing composition of claim 1 wherein the organic solvent is 30.0% to 95.0% of the total weight of the color-changing composition.

8. The color-changing composition of claim 1 wherein the desensitizer comprises tetraethyl ammonium acetate.

9. The color-changing composition of claim 1 wherein the tetraalkyl ammonium carboxylate is selected from the group consisting of tetraethyl ammonium acetate, tetramethyl ammonium acetate, tetrabutyl ammonium acetate and combinations thereof.

10. The color-changing composition of claim 1 wherein the tetraalkyl ammonium hydroxide is selected from the group consisting of tetraethyl ammonium hydroxide, tetramethyl ammonium hydroxide, tetrabutyl ammonium hydroxide and combinations thereof.

11. The color-changing composition of claim 1 wherein the tetraalkyl ammonium halide is selected from the group consisting of tetraethyl ammonium chloride, tetramethyl ammonium fluoride, tetrabutyl ammonium bromide and combinations thereof.

12. The color-changing composition of claim 1 wherein the color-developer comprises bisphenol A, zinc chloride, zinc salicylate, phenol resins or combinations thereof.

13. The color-changing composition of claim 1 wherein the leuco dye comprises phthalide leuco dye, triarylmethane leuco dye, fluoran leuco dye or combinations thereof.

14. A color-changing material comprising:
    a substrate having a color-changing composition disposed thereon wherein the color-changing composition comprises
        a leuco dye;
        a color-developer;
        a desensitizer; and
        a binder;
        wherein the desensitizer comprises tetraalkyl ammonium carboxylate, tetraalkyl ammonium hydroxide, tetraalkyl ammonium halide or combinations thereof.

15. The color-changing material of claim 14 wherein the substrate comprises a nonwoven material.

16. A disposable absorbent article comprising an absorbent core and an outer cover adjacent the absorbent core wherein the outer cover comprises the color-changing material of claim 14.

17. The color-changing material of claim 14 comprising a substrate having a color-changing composition disposed thereon, the color-changing composition having a wet state and a dry state, wherein in the wet state the color-changing composition comprises:
    the leuco dye in the amount of 0.1% to 20.0% of the total weight of the color-changing composition;
    the color-developer in the amount of 0.1% to 17.0% of the total weight of the color-changing composition;

the desensitizer in the amount of 3.0% to 25.0% of the total weight of the color-changing composition;

the binder in the amount of 1.0% to 60.0% of the total weight of the color-changing composition; and an organic solvent in the amount of 30.0% to 95.0% of the total weight of the color-changing composition, and in the dry state, the organic solvent is about 0.0% of the total weight of the color-changing composition.

18. A disposable absorbent article having an absorbent core adjacent an outer cover and a color-changing composition disposed there between, the color-changing composition comprising:

a leuco dye;

a color-developer;

a desensitizer, wherein the desensitizer comprises tetraethyl ammonium acetate, tetramethyl ammonium acetate, tetrabutyl ammonium acetate or combinations thereof; and a binder.

* * * * *